US008831714B2

(12) United States Patent
Lin et al.

(10) Patent No.: US 8,831,714 B2
(45) Date of Patent: Sep. 9, 2014

(54) APPARATUS AND METHOD FOR HEART FAILURE INDICATION BASED ON HEART RATE, ONSET AND TACHYARRHYTHMIA

(75) Inventors: Yayun Lin, St. Paul, MN (US); Shelley M. Cazares, Minneapolis, MN (US); Donald L. Hopper, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1915 days.

(21) Appl. No.: 11/744,952

(22) Filed: May 7, 2007

(65) Prior Publication Data

US 2008/0281370 A1 Nov. 13, 2008

(51) Int. Cl.
*A61B 5/04* (2006.01)

(52) U.S. Cl.
USPC .............................................. 600/515; 607/9

(58) Field of Classification Search
USPC ................... 600/515, 518, 519; 607/4, 14, 15
See application file for complete search history.

(56) References Cited

U.S. PATENT DOCUMENTS

| | | | |
|---|---|---|---|
| 5,184,615 A * | 2/1993 | Nappholz et al. ............. | 607/14 |
| 6,045,513 A | 4/2000 | Stone et al. | |
| 6,102,874 A | 8/2000 | Stone et al. | |
| 6,190,324 B1 | 2/2001 | Kieval et al. | |
| 6,280,409 B1 | 8/2001 | Stone et al. | |
| 6,336,903 B1 | 1/2002 | Bardy | |
| 6,424,865 B1 | 7/2002 | Ding | |
| 6,636,762 B2 * | 10/2003 | Begemann ..................... | 600/519 |
| 6,804,656 B1 | 10/2004 | Rosenfeld et al. | |
| 6,811,537 B2 | 11/2004 | Bardy | |
| 6,908,437 B2 | 6/2005 | Bardy | |
| 7,127,290 B2 * | 10/2006 | Girouard et al. ............... | 607/17 |
| 7,171,271 B2 | 1/2007 | Koh et al. | |
| 2002/0099302 A1 | 7/2002 | Bardy | |
| 2003/0097153 A1 * | 5/2003 | Bardy et al. ..................... | 607/5 |
| 2003/0100925 A1 | 5/2003 | Pape et al. | |
| 2004/0147982 A1 | 7/2004 | Bardy | |
| 2004/0215238 A1 | 10/2004 | van Dam et al. | |
| 2004/0230127 A1 | 11/2004 | Bardy | |
| 2005/0234352 A1 | 10/2005 | Bardy | |
| 2005/0256545 A1 | 11/2005 | Koh et al. | |
| 2006/0167516 A1 | 7/2006 | Kjellstrom et al. | |
| 2007/0191895 A1 * | 8/2007 | Foreman et al. ............... | 607/14 |
| 2007/0239043 A1 * | 10/2007 | Patel et al. ..................... | 600/508 |

OTHER PUBLICATIONS

Arzbaecher et al., "Automatic Tachycardia Recognition", 1984, Pace, vol. 7, p. 541-547.*
Yusuf et al., "Sinus tachyarrhythmias and the specific bradycardic agents: a marriage made in heaven?", 2003, J Cardiovasc Pharmacol Ther., vol. 8, p. 85-88.*

(Continued)

*Primary Examiner* — Carl H Layno
*Assistant Examiner* — Erica Lee
(74) *Attorney, Agent, or Firm* — Schwegman, Lundberg & Woessner, P.A.

(57) ABSTRACT

An indication of an actual or potential heart failure condition is computed. One example includes monitoring a first heart rate preceding a first onset of a first sinus tachyarrhythmia episode. Upon detecting the first sinus tachyarrhythmia episode, the indication is automatically provided using information about the first heart rate and how quickly the first onset occurs.

31 Claims, 7 Drawing Sheets

(56) References Cited

OTHER PUBLICATIONS

Merriam-Webster Online Dictionary, Main Entry: "congestive heart failure", Date: 1930, "www.merriam-webster.com/dictionary/congestive+heart+failure".*

Willems, Rik, et al., "Nonexcitatory stimulation as a novel treatment for heart failure: cause for excitement?", *European Heart Journal 25*, (2004), 626-628.

Brady, P. A., et al., "Inappropriate sinus tachycardia, postural orthostatic tachycardia syndrome, and overlapping syndromes.", *Pacing Clin Electrophysiol.*, 28(10), (2005), 1112-21.

Kouakam, C., et al., "Effect of elevated heart rate preceding the onset of ventricular tachycardia on antitachycardia pacing effectiveness in patients with implantable cardioverter defibrillators.", *American Journal of Cardiology*, 92(1), (Jul. 1, 2003), 26-32.

* cited by examiner

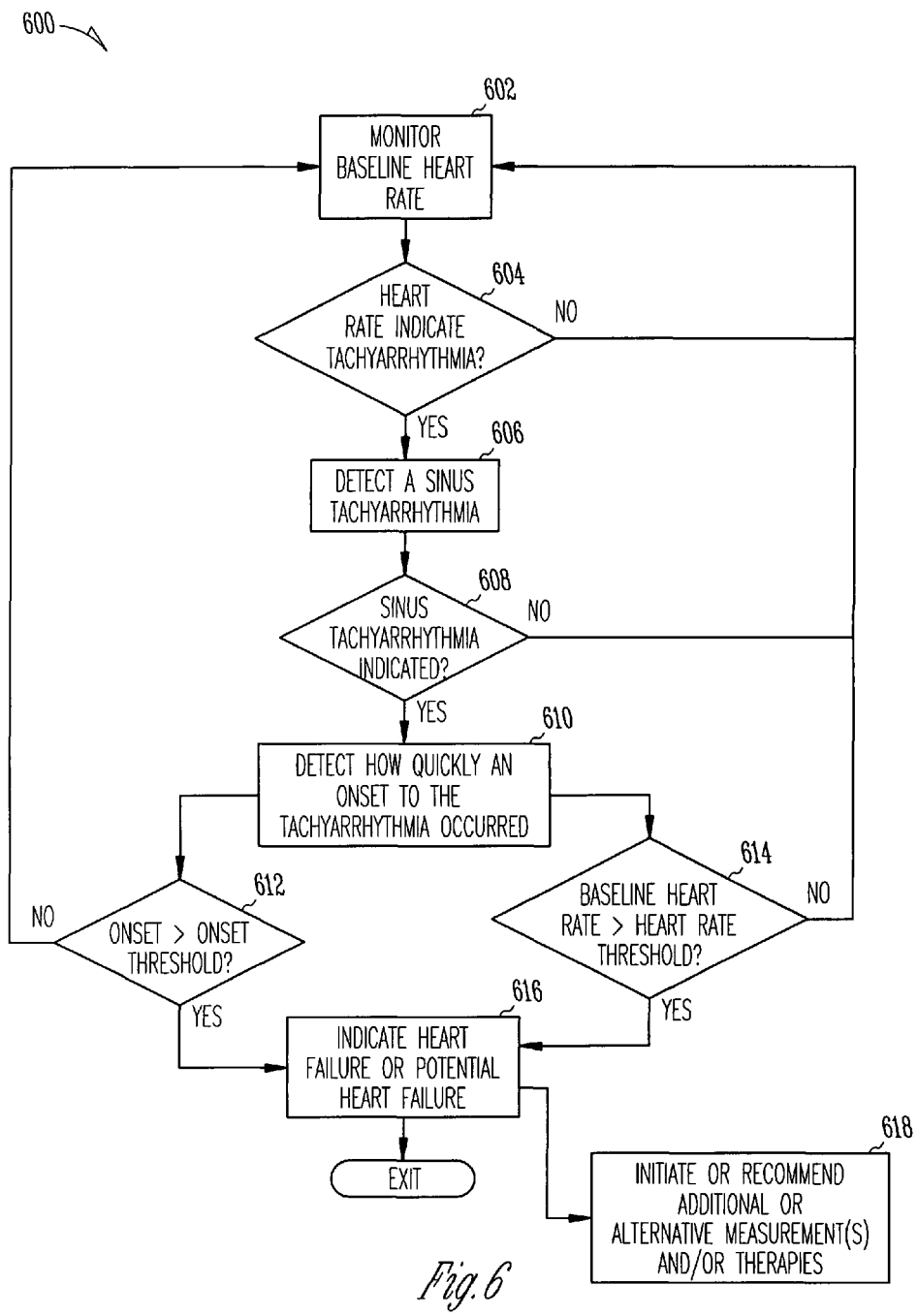

APPARATUS AND METHOD FOR HEART FAILURE INDICATION BASED ON HEART RATE, ONSET AND TACHYARRHYTHMIA)

APPARATUS AND METHOD FOR HEART FAILURE INDICATION BASED ON HEART RATE, ONSET AND TACHYARRHYTHMIA

TECHNICAL FIELD

This patent document pertains generally to cardiac rhythm or function management devices, and more particularly, but not by way of limitation, to a system and method for providing a heart failure indication based on heart rate, onset, and tachyarrhythmia.

BACKGROUND

Heart failure, which is also called congestive heart failure (CHF) or congestive cardiac failure (CCF), is a condition that can result from any structural or functional cardiac disorder that impairs pumping blood with the heart, or filling the heart with blood. Heart failure is often undiagnosed. This is due, in part, to a shortage of recognized relationships between one or more symptoms. Practitioners often are not permitted to perform studies intended to detect heart failure without a precursor indication from the patient that heart failure testing is merited. An additional aspect of the problem is that there are a limited number of useful indicators available that can communicate to a practitioner that heart failure may be present, and that further measurements should be performed.

Additionally, there is a shortage of tools to monitor the success of heart failure treatments. Because there is a shortage of diagnostics which demonstrate actual or potential heart failure, the efficacy of ongoing treatment is not always understood.

OVERVIEW

In Example 1, a method comprises monitoring a first heart rate and detecting a first sinus tachyarrhythmia episode preceded by the first heart rate. When the first sinus tachyarrhythmia episode is detected, the method comprises determining how quickly a first onset to the first sinus tachyarrhythmia episode occurs and automatically providing an indication of an actual or potential heart failure condition using information about the first heart rate and how quickly the first onset to the first sinus tachyarrhythmia episode occurs.

In Example 2, the method of Example 1 can be optionally configured to such that automatically providing an indication of an actual or potential heart failure condition comprises using an indication that the first heart rate exceeds a specified threshold heart rate.

In Example 3, the methods of Examples 1-2 can be optionally configured such that the first heart rate immediately precedes first onset of the first sinus tachyarrhythmia episode.

In Example 4, the methods of Examples 1-3 can be optionally configured such that the automatically providing the indication of the heart failure condition includes also using a clinically-obtained functional classification of the patient to determine the indication of the heart failure condition.

In Example 5, the methods of Examples 1-4 can be optionally configured such that the system includes initiating or recommending a measurement of a respiratory rate of the patient in response to the indication of the heart failure condition.

In Example 6, the methods of Examples 1-5 can be optionally configured such that the system includes initiating or recommending a measurement of an ejection fraction of the patient in response to the indication of the heart failure condition.

In Example 7 the methods of Examples 1-6 can be optionally configured such that the system includes initiating or recommending a measurement of a B-type natriuretic peptide (BNP) of the patient in response to the indication of the heart failure condition.

In Example 8 the methods of Examples 1-7 can be optionally configured such that the system includes initiating or recommending a measurement of a QRS width of the patient in response to the indication of the heart failure condition.

In Example 9 the methods of Examples 1-8 can be optionally configured such that the system includes initiating or recommending a measurement of a heart rate variability of the patient in response to the indication of the heart failure condition.

In Example 10 the methods of Examples 1-9 can be optionally configured such that the system includes measuring an indication of autonomic balance of the patient and such that the automatically providing the indication of the heart failure condition includes also using the measured indication of autonomic balance to determine the indication of the heart failure condition.

In Example 11 the methods of Examples 1-10 can be optionally configured such that the system includes measuring heart rate variability of the patient and such that the automatically providing the indication of the heart failure condition includes also using the measured heart rate variability to determine the indication of the heart failure condition.

In Example 12 the methods of Examples 1-11 can be optionally configured such that automatically providing an indication of an actual or potential heart failure condition uses an indication that the first onset occurs more quickly than a specified onset threshold.

In Example 13 the methods of Examples 1-12 can be optionally configured such that the system includes detecting a second sinus tachyarrhythmia episode preceded by a second heart rate, determining a combined indication of the first and second heart rates, determining a combined indication of how quickly onsets of the first and second sinus tachyarrhythmia episodes occur and automatically providing the indication of the heart failure condition when the combined indication of the onsets occurs more quickly than the specified onset threshold and the combined indication of the first and second heart rates exceeds the specified threshold heart rate.

In Example 14 the methods of Examples 1-13 can be optionally configured such that the determining how quickly the first onset occurs includes determining an amount of change between first and second cardiac cycle intervals and can be optionally configured such that the system includes computing the indication that the first onset occurs more quickly than the specified threshold by comparing the amount of change between the first and second cardiac cycles to the specified threshold.

In Example 15 the methods of Examples 1-14 can be optionally configured such that the system includes monitoring a degree of pacing of a ventricle and automatically providing the indication of the heart failure condition at least in part in response to at least one indication that the degree of pacing of the ventricle exceeds a specified degree of pacing threshold.

In Example 16 the methods of Examples 1-15 can be optionally configured such that the system includes automatically initiating, recommending, or monitoring a first cardiac resynchronization therapy.

In Example 17 the methods of Examples 1-16 can be optionally configured such that the system includes automatically providing a recommendation for a second cardiac resynchronization therapy.

In Example 18, an apparatus comprises a first heart rate monitor circuit, a sinus tachyarrhythmia episode detection circuit, a sinus tachyarrhythmia onset detector circuit, configured to determine how quickly a first onset to a first sinus tachyarrhythmia episode occurs and a heart failure indication detector circuit, coupled to at least one of the heart rate monitor circuit, the sinus tachyarrhythmia episode detection circuit, and the sinus tachyarrhythmia onset detector circuit. The apparatus is configured such that the heart failure indication detector circuit is configured to indicate an actual or potential heart failure condition, when the first sinus tachyarrhythmia episode is detected, by using information about a first heart rate preceding the first sinus tachyarrhythmia episode and information about how quickly the first onset to the first sinus tachyarrhythmia episode occurs.

In Example 19 the apparatus of Examples 18 can be optionally configured such that the heart rate monitor circuit is configured to be coupled to at least one external electrode.

In Example 20 the apparatus of Examples 18-19 can be optionally configured to include a sinus tachyarrhythmia onset comparator circuit, configured to determine whether how quickly the first onset occurs exceeds a specified onset threshold.

In Examples 21 the apparatus of Examples 18-20 can be optionally configured such that the heart failure indication detector circuit is configured to indicate an actual or potential heart failure condition at least in response to at least one indication that the first onset occurs more quickly than the specified onset threshold.

In Examples 22 the apparatus of Examples 18-21 can be optionally configured to include a heart rate comparator circuit, configured to determine whether a first heart rate preceding the first onset of the first sinus tachyarrhythmia episode exceeds a specified heart rate threshold.

In Examples 23 the apparatus of Examples 18-22 can be optionally configured such that the apparatus includes an implantable medical device.

In Examples 24 the apparatus of Examples 18-23 can be optionally configured such that the heart rate monitor circuit is configured to be coupled to at least one implantable electrode.

In Examples 25 the apparatus of Examples 18-24 can be optionally configured such that the implantable medical device includes a wireless communication circuit configured to communicate information about the indicator to a local or remote external user interface.

In Examples 26 the apparatus of Examples 18-25 can be optionally configured such that the implantable medical device includes a cardiac rhythm management device including an electrostimulation delivery circuit that is configured to be controlled using information about the indicator.

In Example 27, an apparatus comprises a heart rate monitor circuit, a sinus tachyarrhythmia episode detection circuit, means for determining how quickly a first onset to the first sinus tachyarrhythmia episode occurs and means for automatically providing an indication of an actual or potential heart failure condition using an indication that the first onset occurs more quickly than a specified onset threshold together with an indication that a first heart rate exceeds a specified threshold heart rate, such that the first heart rate precedes the first onset to the first sinus tachyarrhythmia episode.

In Example 28 the apparatus of Example 27 can be optionally configured such that the means for determining how quickly a first onset to the first sinus tachyarrhythmia episode occurs includes a heart rate comparator circuit, configured to determine whether a first heart rate preceding the first onset of the first sinus tachyarrhythmia episode exceeds a specified threshold heart rate value.

In Example 29 the apparatus of Examples 27-28 can be optionally configured such that the means for automatically providing an indication of a potential heart failure condition includes an indicator, coupled to at least one of the sinus tachyarrhythmia onset detector circuit and the sinus tachyarrhythmia rate comparator circuit, the indicator configured to indicate the actual or potential heart failure condition at least in response to at least one indication that the first onset occurs more quickly than a specified onset threshold together with at least one indication the first heart rate exceeds a specified threshold heart rate.

This is an overview of some of the teachings of the present application and not intended to be an exclusive or exhaustive treatment of the present subject matter details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various examples discussed in the present document.

FIG. 6 is an example of a method for determining heart failure or potential failure using at least on the rate of onset to tachyarrhythmia, a heart rate, and detection of a sinus tachyarrhythmia.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present application includes method and apparatus for the indication of actual or potential heart failure. Included are implantable devices, as well as external devices. Devices and methods that store indications are included, as are devices and methods that communicate indications real-time. The present examples include devices and methods that provide an indication of an actual or potential heart failure condition based on one or more of: the existence of a tachyarrhythmia, a measured heart rate preceding the tachyarrhythmia onset and how quickly the onset to the tachyarrhythmia occurs.

Figure 1:
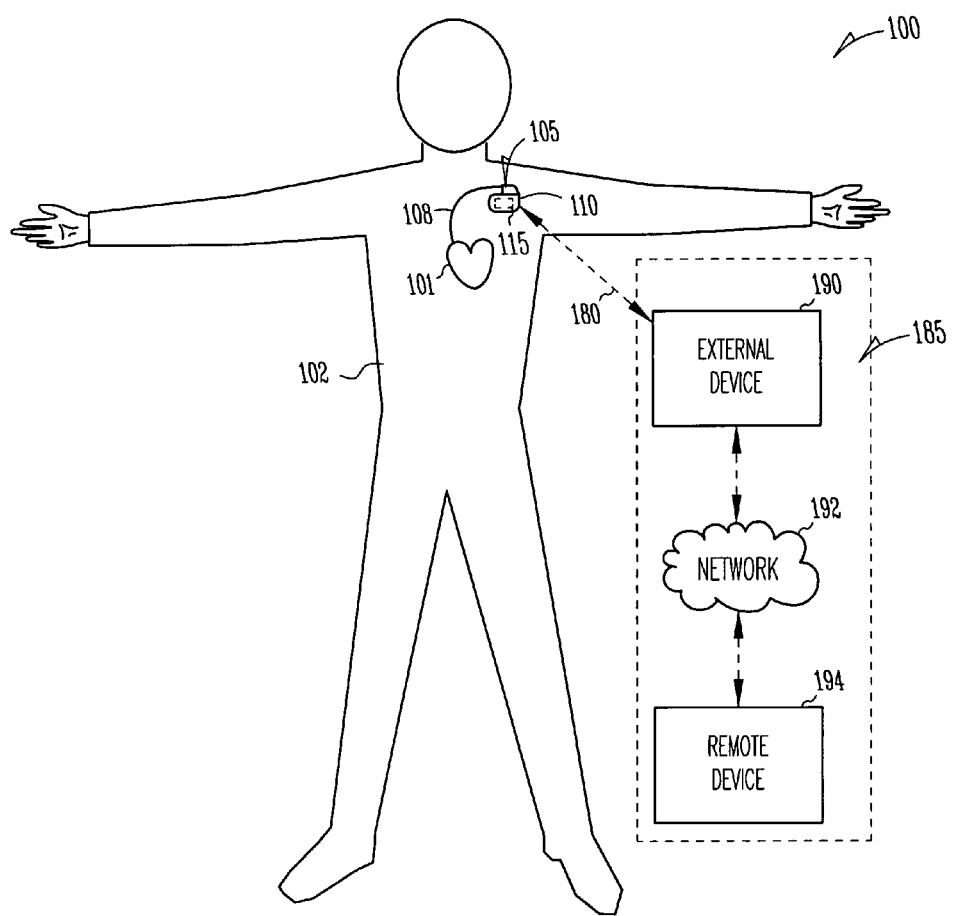
FIG. 1 is a schematic drawing illustrating generally an example of portions of a system that can be used to detect heart failure, and portions of an environment in which it is used.

FIG. 1 is an illustration of an example of a CRM system 100 and portions of an environment in which CRM system 100 is used. CRM system 100 includes an implantable system 105, an external system 185, and a telemetry link 180 providing for communication between implantable system 105 and external system 185.

Implantable system 105 includes, among other things, implantable medical device 110 and lead system 108. In various examples, implantable medical device 110 is an implantable CRM device including one or more of a pacer, a cardioverter/defibrillator, a cardiac resynchronization therapy (CRT) device, a cardiac remodeling control therapy (RCT) device, a neurostimulator, a drug delivery device or a drug delivery controller, and a biological therapy device.

As illustrated in FIG. 1, implantable medical device 110 is implanted in a body 102. In various examples, lead system 108 includes implantable electrodes for sensing physiological signals. Lead system 108 additionally includes implantable electrodes for delivering pacing pulses, cardioversion/defibrillation shocks, neurostimulation pulses, or pharmaceutical or other substances in additional examples. In some examples, lead system 108 includes one or more pacing-sensing leads each including at least one electrode placed in or on a heart 101 for sensing electrogram or delivering pacing pulses. In another example, lead system 108 includes one or more neurostimulation-sensing leads each including at least one electrode placed on a nerve of the autonomic nervous system for sensing neural signals and delivering neurostimulation pulses. In another example, lead system 108 includes one or more pacing-sensing leads and one or more neurostimulation-sensing leads to synchronize neurostimulation with intrinsic activities of heart 101 or pacing.

In one example, external system 185 is a patient management system including a local external device 190, a network 192, and a remote device 194. Local external device 190 is within the vicinity of implantable medical device 110 and communicates with implantable medical device 110 bi-directionally via telemetry link 180. Remote device 194 is in a remote location and communicates with external device 190 bi-directionally via network 192, thus allowing a user to monitor and treat a patient from a distant location. In another example, external system 185 includes a programmer communicating with implantable medical device 110 bi-directionally via telemetry link 180.

System 100 includes a monitoring system 115 that detects an actual or potential heart failure condition using, in part, onset to tachyarrhythmia and heart rate. Some examples monitor a tachyarrhythmia and classify the tachyarrhythmia as a sinus tachyarrhythmia (ST). Some examples are configured to distinguish between a ventricular tachyarrhythmia (VT), a supraventricular tachyarrhythmia (SVT), and an ST.

The distribution of monitoring system 115 in system 100 can vary. In one example, as illustrated in FIG. 1, implantable medical device 110 includes the entire system 115. This allows implantable system 105 to monitor for heart failure without communicating to external system 185. In another example, implantable medical device 110 and external system 185 each include portions of system 115. Heart failure information is collected when implantable medical device 110 and external system 185 are communicatively coupled via telemetry link 180.

Figure 2:
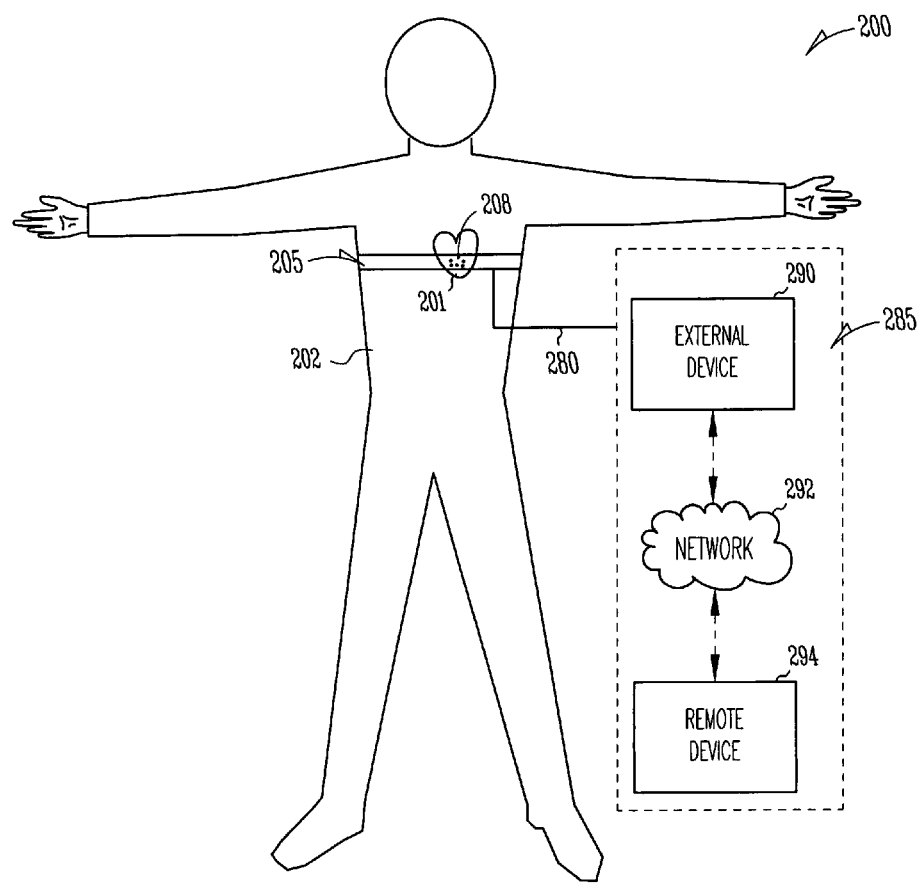
FIG. 2 is a schematic drawing illustrating generally an example of portions of a system that can be used to detect heart failure, and portions of an environment in which it is used.

FIG. 2 is an illustration of an example of a monitoring system 200 and portions of an environment in which monitoring system 200 is used. System 200 includes an external electrode system 205, an external system 285, and a link 280 providing for communication between external electrode system 205 and external system 285.

External electrode system 205 includes, among other things, an electrode 208. In some instances, external electrode system 205 includes an externally worn patch. Some examples include an electrode capable of transmitting energy to a body 202. Certain examples include an electrode used to monitor electrical pulses presented by a body 202. In various examples, external electrode system 205 is able to provide various therapies, including, but not limited to, one or more of pacing, cardioversion/defibrillation, cardiac resynchronization therapy (CRT), cardiac remodeling control therapy (RCT), neurostimulation, drug delivery, and biological therapy.

In various examples, external electrode system 205 includes electrodes for sensing one or more physiological signals. External electrode system 205 can include electrodes for delivering one or more of pacing pulses, cardioversion/defibrillation shocks, neurostimulation pulses, or pharmaceutical or other substances in certain examples.

In certain examples, external electrode system 205 includes one or more pacing or sensing electrodes each including at least one electrode placed near a heart 201 for sensing an electrogram or delivering pacing pulses. In certain examples, external electrode system 205 includes one or more neurostimulation-sensing electrodes each including at least one electrode placed on or near a nerve of the autonomic nervous system for sensing one or more neural signals or delivering neurostimulation pulses. In certain examples, external electrode system 205 includes one or more pacing-sensing electrodes and one or more neurostimulation-sensing leads to synchronize neurostimulation with intrinsic activity of heart 202 or pacing.

In certain examples, external system 285 is a patient management system including an external device 290, a network 292, and a remote device 294. External device 290 is within the vicinity of external electrode system 205 and communicates with external electrode system 205 bi-directionally via a wired or wireless communication link 280. In some examples, link 280 includes wireless telemetry. In additional examples, link 280 is a wired link. Remote device 294 is generally in a remote location and communicates with external device 290 bi-directionally via network 292, thus allowing a user to monitor and treat a patient from a distant location.

System 200 includes an external system 285 and an external electrode system 205 that detects a heart failure condition or a potential heart failure condition using, in part, onset and heart rate. Some examples monitor how quickly the onset to a tachyarrhythmia occurs. Some examples monitor heart rate and monitor the occurrence of a tachyarrhythmia, and classify a tachyarrhythmia as a sinus tachyarrhythmia (ST). Various examples are configured to distinguish between a ventricular tachyarrhythmia (VT), a supraventricular tachyarrhythmia (SVT), and an ST.

Figure 3:
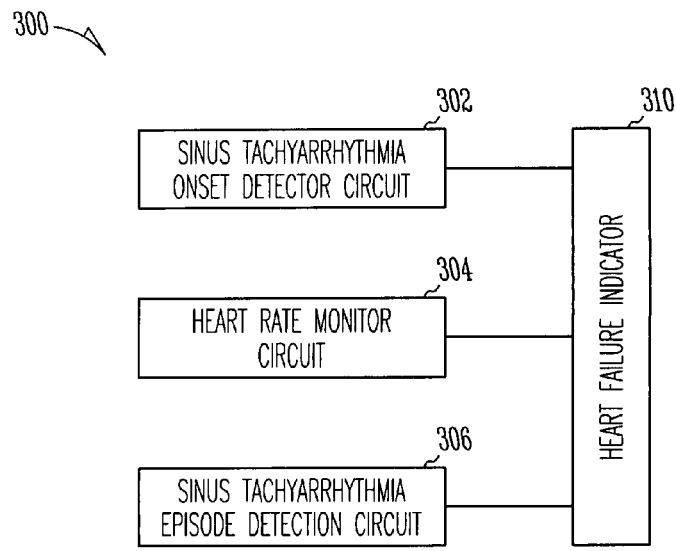
FIG. 3 is an example of a block diagram of an apparatus which indicates actual or potential heart failure based at least on the rate of onset to tachyarrhythmia, a heart rate, and detection of a sinus tachyarrhythmia.

FIG. 3 is an example of a block diagram of a monitor 300 that indicates actual or potential heart failure based at least on one or more of how detection of a sinus tachyarrhythmia, how quickly the onset to tachyarrhythmia occurs and a heart rate preceding the onset. In some instances, a sinus tachyarrhythmia onset detector circuit 302 is in communication with the heart failure indicator circuit 310. The sinus tachyarrhythmia onset detector circuit 302 provides the heart failure indicator circuit 310 with information relating to how quickly onset to tachyarrhythmia occurs. Heart rate monitor circuit 304 is in communication with a heart failure indicator circuit 310. The heart rate monitor circuit 304 provides heart rate information to the heart failure indicator circuit 310. The example also includes a sinus tachyarrhythmia episode detection circuit 306 in communication with the heart failure indicator circuit 310. The sinus tachyarrhythmia episode detection circuit 306 provides information indicative of one or more detected tachyarrhythmia episodes to the heart failure indicator circuit 310, in various examples.

Heart failure indicator circuit 310 is configured to indicate heart failure or potential heart failure based on communication with the sinus tachyarrhythmia onset detector circuit 302, in some instances. The heart failure indicator circuit 310 is configured in the example to indicate heart failure or potential heart failure based on communication with the heart rate monitor circuit 304. In various examples, the heart failure indicator circuit 310 is configured to indicate actual or potential heart failure based on communication with the sinus tachyarrhythmia episode detection circuit 306.

Circuits of the present examples may be implemented using a combination of hardware and software. For example, one or more elements may be implemented using an application-specific circuit constructed to perform one or more particular functions. Some examples use a general-purpose circuit programmed to perform such function(s). Such a general-purpose circuit includes, but is not limited to, a microcontroller or a portion thereof, a microcontroller or portions thereof, and a programmable logic circuit or a portion thereof. The controller can include a microcontroller, controller, digital signal controller, or other processing components, and may be integrated into a single component or partitioned into more than one component. Examples are included in which all or a portion of monitor 300 is implanted.

Figure 4:
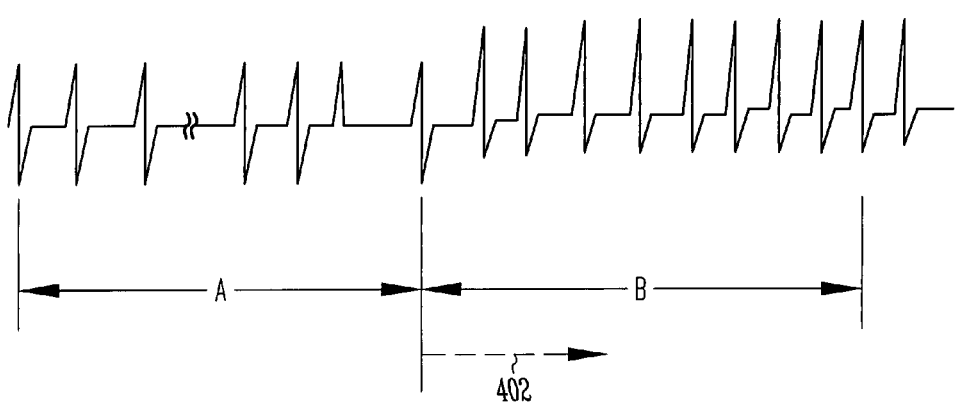
FIG. 4 is an example of a measured cardiac cycle, according to one example.

FIG. 4 is an example of a measured cardiac cycle 400, according to one example. The cardiac cycle includes a first window A and a second window B. The first window A includes a baseline heart rate. In various embodiments, the baseline heart rate is a normal resting heart rate. At least one interval is needed to establish a baseline heart rate in window A, but more intervals may be used. Baseline heart rate can be averaged across multiple intervals. Additionally, baseline heart rate can be determined using other mathematical operations.

The second window B includes a tachyarrhythmia and an onset to a tachyarrhythmia 402. In various examples, the present subject matter monitors baseline heart rate intervals for a set period of time. Some examples use one minute, but the present subject matter is not so limited. The present subject matter establishes a baseline threshold heart rate and divides the set period of time by the baseline threshold rate to get a baseline threshold interval. In some embodiments, the baseline threshold rate is 110 beats per minute, but the present subject matter includes other rates. In various embodiments, a set period of time of one minute is divided by a baseline threshold rate of 110 beats per minute to get an interval threshold of 545 ms. If an interval is less than this threshold, it is indicated to be fast. In various embodiments, if a certain number of intervals are indicated to be fast, tachyarrhythmia is indicated. Some embodiments require that 8 of 10 intervals be fast, but the technology is not so limited. If a tachyarrhythmia is indicated, various examples measure onset to tachyarrhythmia.

Window B includes a tachyarrhythmia. Some examples categorize the tachyarrhythmia. Examples include a tachyarrhythmia which is a sinus tachyarrhythmias. Determination of a sinus tachyarrhythmia can include, but is not limited to, one or more of measuring rate, morphology, or other parameters as discussed herein. Other tachyarrhythmias may be used as disclosed herein.

In certain examples, window B includes an onset to tachyarrhythmia 402 measure. Onset to tachyarrhythmia 402 includes two or more of the beats extending from left to right starting from the left side of window B. The rate of change of the intervals which occur at this position are determinative of the onset rate. In various embodiments, the onset includes one or more ectopic intervals which precede window B. In examples where ectopic intervals do not precede window B, onset is constrained to the left side of window B.

In various embodiments, an onset determination is a measure of how quickly onset to a tachyarrhythmia occurs. Such a measurement can be reflected in time, in a percentage change, or another way. Various mathematical operators are used in different examples, including, but not limited to, averaging over two or more cycles.

Certain examples measure these two windows and indicate an actual or potential heart failure based on these two windows. Some examples use less or more windows. Some examples include one or more of a heart rate window. Some examples include one or more of an onset window. Some examples include one or more of a tachyarrhythmia window. For example, some designs measure multiple onsets, but do not measure multiple heart rates. Examples including windows which are not immediately adjacent to one another are included. Additional variations are possible.

Figure 5:
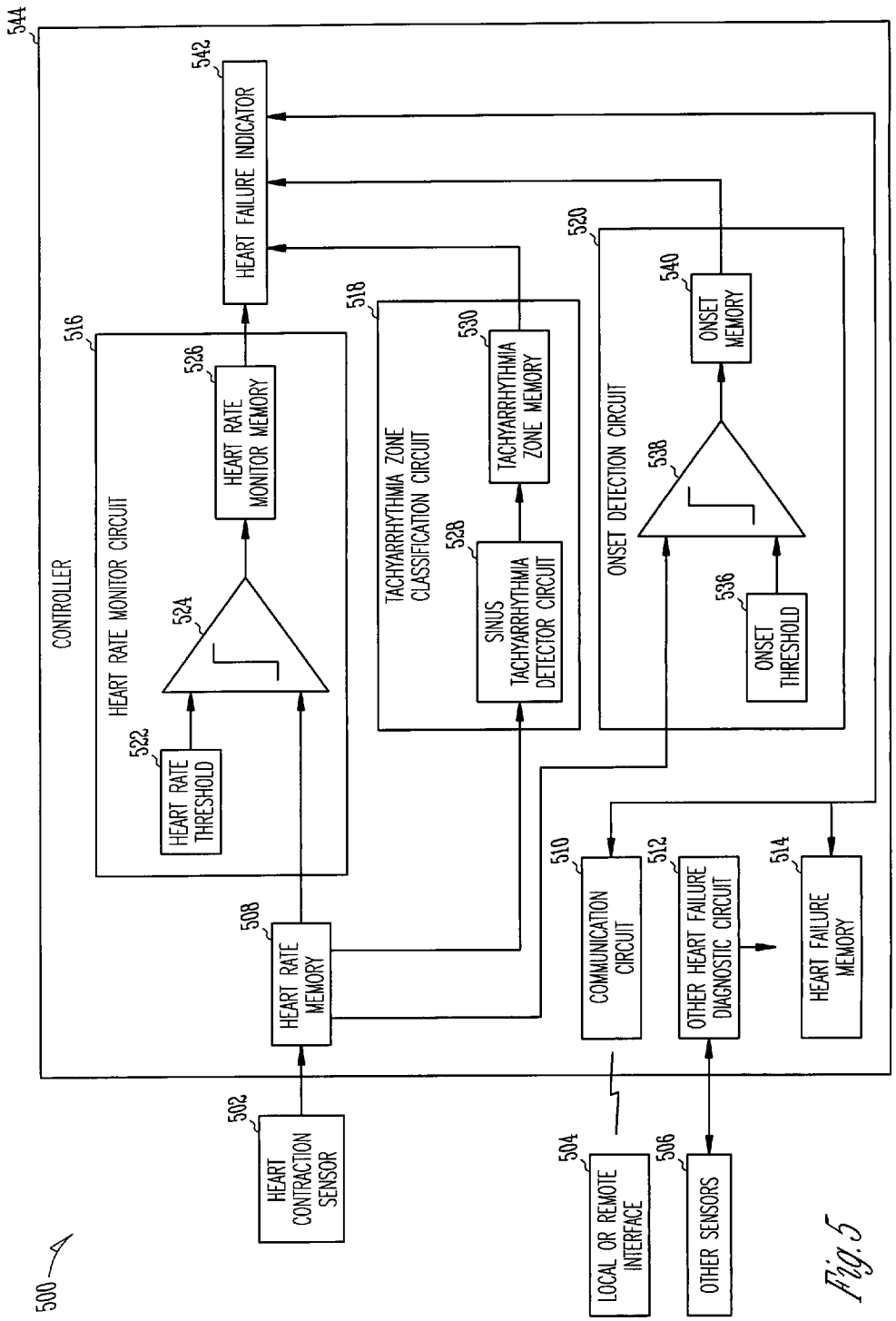
FIG. 5 is an example of a block diagram of an apparatus which indicates actual or potential heart failure based at least on the rate of onset to tachyarrhythmia, a heart rate, and detection of a sinus tachyarrhythmia.

FIG. 5 is an example of a block diagram of an apparatus that indicates actual or potential heart failure based at least in part on one or more of the rate of onset to a tachyarrhythmia, a heart rate, and detection of a tachyarrhythmia. The monitor 500 includes a controller 544 that is coupled to the heart contraction sensor 502. The controller and other circuits may be implemented using a combination of hardware and software.

In various examples, the heart contraction sensor 502 communicates information to the controller 544. In some instances, heart contraction sensor 502 includes an implantable intrinsic cardiac signal sensor to peak-detect, level-detect, or otherwise detect intrinsic depolarizations indicative of heart contractions. In some instances, such detection involves frequency-selective filtering. In other examples, the heart contraction sensor 502 includes an implantable impedance sensor to detect heart contractions, such as via variations in a transthoracic or intracardiac impedance signal. In still other examples, the heart contraction sensor 502 can detect information indicative of heart contractions from an acceleration signal, a sound signal, or a blood pressure signal. Information from multiple signals or sources can also be combined to detect heart contractions. Additional or alternative examples include an external heart contraction sensor that is adapted to monitor heart rate intervals.

In this example, the monitor 500 includes a heart rate memory 508. The heart rate memory is configured to store information about one or more heart beat intervals. In some examples, the heart rate memory stores at least approximately 26 intervals. In some examples, the heart rate memory stores more than approximately 26 intervals. Some embodiments store approximately 32 intervals.

In some examples, a heart rate monitor circuit 516 is in communication with a heart failure indicator circuit 542. The heart rate monitor circuit 516 provides heart rate information to the heart failure indicator circuit 542. In various examples, the heart rate monitor circuit 516 includes a heart rate monitor comparator 524 that is configured to compare heart rate information taken from one or both of the heart contraction sensor 502 and the heart rate memory 508 to a heart rate threshold 522. Some examples include a heart rate monitor memory 526 that stores information communicated by the heart rate monitor comparator 524. Various examples include a heart failure indicator 542 that is configured to automatically provide an indication of an actual or potential heart failure condition based at least on an indication that the first heart rate exceeds the specified threshold heart rate 522.

The example includes a tachyarrhythmia detector such as a tachyarrhythmia zone classification circuit 518 that is in communication with a heart failure indicator circuit 542. The tachyarrhythmia zone classification circuit 518 provides tachyarrhythmia information to the heart failure indicator circuit 542. The tachyarrhythmia zone classification circuit is configured to provide tachyarrhythmia information to the heart failure indicator 542. Examples of output of the tachyarrhythmia zone classification circuit 518 include, but are not limited to, an indication of a ventricular tachyarrhythmia (VT), an indication of a supraventricular tachyarrhythmia (SVT), and an indication of a sinus tachyarrhythmia (ST). One or more of a variety of tachyarrhythmia classification schemes are used in some instances. Tachyarrhythmia classification circuits can include, but are not limited to, morphology circuits, heart rate circuits, premature ventricular complexes (PVCs) filter circuits, and other circuits.

In various examples, the tachyarrhythmia zone classification circuit 518 includes a sinus tachyarrhythmia detector circuit 528. The sinus tachyarrhythmia detector circuit 528 is configured to determine whether or not a tachyarrhythmia is a sinus tachyarrhythmia. The sinus tachyarrhythmia detector circuit 528 can output an indication of a sinus tachyarrhythmia to the heart failure indicator 542 in some examples. Some examples include a tachyarrhythmia zone memory 530 that stores information communicated by the sinus tachyarrhythmia detector circuit 528. In some examples, the heart failure indicator 542 uses heart rate information from the tachyarrhythmia zone memory 530 in providing an indication of an actual or potential heart failure condition.

According to the example, an onset detection circuit 520 is in communication with a heart failure indicator circuit 542. The onset detection circuit 520 provides heart rate information to the heart failure indicator circuit 542. In various examples, the onset detection circuit 520 includes an onset detection comparator 538 that is configured to compare onset information derived from heart rate information taken from one or both of the heart contraction sensor 502 and the heart rate memory 508 to an onset threshold 536. Various examples include a heart failure indicator 542 that is configured to automatically provide an indication of an actual or potential heart failure condition based at least on an indication that the a measured onset to a tachyarrhythmia exceeds the specified onset threshold 536. Some examples include an onset memory 540 that stores information communicated by the onset detection comparator 538. In some examples, the heart failure indicator 542 uses onset to tachyarrhythmia information from the onset memory 540 in providing an indication of an actual or potential heart failure condition.

In some instances, all or a portion of controller 544 are located in an implantable medical device. In additional or alternative examples, all or part of controller 544 is located in a device external to the patient, and communication with the heart contraction sensor uses wireless or wired communications.

The monitor 500 can additionally or alternatively include one or more implantable or external other sensors 506, such as an acceleration sensor to detect patient activity, a position sensor to detect patient posture, a heart sound sensor to detect patient heart sounds, a weight sensor to sense patient weight, an impedance sensor to detect thorax or heart impedance or any other suitable sensor for detecting one or more physiologic signals. In various examples, the controller 544 includes a heart failure diagnostic circuit 512 that is in communication with other sensors 506. The other heart failure diagnostic circuit 512 communicates other indicia of heart failure to heart failure indicator 542. In some examples, such indicia are stored in the heart failure memory.

Heart failure indicia developed by circuits integrated with controller 544 may be stored in heart failure memory 514. Additionally, heart failure diagnosis determined by separate devices may be stored in heart failure memory 514. For example, local or remote interface 504 can communicate with communications circuit 510 to store heart failure information in heart failure memory 514.

In some examples, processor 544 automatically provides an indication of the heart failure condition using a clinically-obtained functional classification of the patient to determine the indication of the heart failure condition in addition to an actual or potential heart failure indication based at least in part on one of the heart rate monitor circuit 516, the tachyarrhythmia zone classification circuit 518, and the onset detection circuit 520. In some instances, a New York Heart Association (NYHA) class is associated with a patient and stored in heart failure memory 514. In some examples, a health care provider inputs NYHA data into processor 544.

Additional examples include measuring an indication of autonomic balance and automatically providing an indication of heart failure using autonomic balance in addition to an actual or potential heart failure indication based at least in part on one of the heart rate monitor circuit 516, the tachyarrhythmia zone classification circuit 518, and the onset detection circuit 520. In some examples, measuring an indication of autonomic balance is performed by processor 544. In additional examples, measuring an indication of autonomic balance is performed external to monitor 500 and communicated with heart failure indicator 542 using local or remote interface 504 and communication circuit 510. In some examples, the measured indication of autonomic balance includes a measured heart rate variability of the patient. In some of these examples, automatically providing the indication of the heart failure condition includes also using the measured heart rate variability to determine the indication of the heart failure condition.

FIG. 6 illustrates an example of a method 600 for determining heart failure or potential heart failure using onset to sinus tachyarrhythmia. Examples include monitoring a first baseline heart rate at 602. At 602, monitoring a first baseline heart rate includes tracking a sequence of heart depolarizations, and determining intervals between successive heart depolarizations. One or more filtering or other signal processing operations are performed in some instances. An example of such an operation used in monitoring a heart rate at 602 includes filtering heart rate information to remove premature ventricular complexes (PVCs). Some examples of monitoring a heart rate at 602 include storing a heart rate in a memory or some other storage device. Some examples of monitoring a heart rate at 602 include displaying a heart rate with a display readable by a practitioner.

The heart rate data can be analyzed to detect whether a heart rate, monitored at 602, indicates that a tachyarrhythmia is occurring at 604. Some examples analyze rate only, while some examples combine heart rate with morphology or other information to detect a tachyarrhythmia. Examples of tachyarrhythmia detection methods includes RHYTHM ID®, OBDE, or ARC. If no tachyarrhythmia is detected at 604, heart rate monitoring continues at 602. Such analysis can be performed by a circuit. Additionally, such analysis can be performed by reading an electrocardiogram (ECG) and applying measurements to the ECG which are indicative tachyarrhythmia or a specific kind of tachyarrhythmia.

If a tachyarrhythmia is detected at 604, various examples classify the tachyarrhythmia, for example, as a VT, a SVT or ST. Techniques discussed herein that are used for detecting tachyarrhythmia can also be used to classify a tachyarrhythmia. At 606, the illustrated example detects whether a sinus tachyarrhythmia is present. Various examples query at 608 whether a sinus tachyarrhythmia is detected. In various examples, if a sinus tachyarrhythmia is detected, the method at 610 analyzes how quickly an onset to the sinus tachyarrhythmia occurred.

Various technique can be used to determine how quickly the onset to the sinus tachyarrhythmia. Some examples compare at 612 a calculated onset (e.g., how quickly the tachyarrhythmia materializes) to a specified onset threshold. In these examples, if a calculated onset is greater than a specified onset threshold, an indication of actual or potential heart failure at 616 may be exhibited. In certain examples, determining how quickly the first onset occurs includes determining an amount of change between successive first and second cardiac cycle intervals. In the example, computing the indication that the first onset occurs more quickly than the specified threshold by comparing the amount of change between the first and second cardiac cycles to the specified threshold. Some examples measure more than two successive cardiac cycles. If an onset meets an onset threshold, some examples indicate an actual or potential heart failure. For example, if an onset is greater than or equal to 17%, certain examples indicate an actual or potential heart failure. Other values are used in some examples.

In some instances, the intervals measured to indicate onset are those that immediately precede a tachyarrhythmia episode. In additional examples, an onset is indicated when a sinus tachyarrhythmia episode that was not preceded by the indicated onset is indicated.

In some examples, an actual or potential heart failure is not indicated unless a 614 heart rate exceeds a heart rate threshold. In the example, the heart rate threshold is 85 beats per minute. In some examples, the heart rate threshold is 110 beats per minute. Other heart rate thresholds are possible. Some examples require only one interval to determine heart rate, while additional examples use multiple intervals. Averages, RMS calculations, or other mathematical operations are used in varying examples.

In the example, when an onset is indicated to satisfy an onset threshold at 612 and the heart rate is indicated to satisfy a heart rate threshold at 614, one of actual or potential heart failure is indicated. In some examples, one of actual or potential heart failure is indicated when multiple sinus tachyarrhythmias are indicated, and for each sinus tachyarrhythmia, how quickly an onset of the sinus tachyarrhythmia occurred exceeds an onset threshold, and for each sinus tachyarrhythmia, a heart rate that precedes the onset of that particular sinus tachyarrhythmia exceeds heart rate threshold.

In various examples, an indicated actual or potential heart failure is combined with one or both of the initiating of a concurrent diagnostic, or the recommendation for performing a concurrent diagnostic at 618. Several diagnostics are used including, but not limited to, measurement of a respiratory rate of the patient, measurement of an ejection fraction of the patient measurement of a B-type natriuretic peptide (BNP) of the patient, measurement of a QRS width of the patient, and measurement of a heart rate variability of the patient. Other diagnostics can additionally be performed. One or more of such indications or recommendations can be stored in an implantable device for later communication to a health car provider. Additionally, one or more of such indications or recommendations can result from measurements triggered by health care providers during a clinical visit. Also, one or more of such indications or measurements can be communicated using a patient management system configured to communicate one or more of such indications or measurements to remote locations via wireless or wired communication. In one example, an indication or recommendation for additional measurements is communicated to a central server and stored for present or future reference by a user.

The heart failure indication obtained using ST detection, how quickly the ST onset occurs, and a pre-onset rate comparison can be combined with another heart failure indication obtained by determining that a degree of pacing of a ventricle exceeds a specified degree of pacing threshold. Such measurements can be performed by a device that monitors alternative or additional indicators of an actual or potential heart failure condition as disclosed herein, but need not be combined with such a device.

One or more of the present heart failure indicators can be used to control a responsive therapy. Examples of responsive therapies can include, but are not limited to, pacing, a cardioversion/defibrillation, cardiac remodeling control therapy (RCT), neurostimulation therapy, drug delivery, and biological therapy. In some examples, monitoring for actual or potential heart failure is performed concurrent to cardiac resynchronization therapy (CRT). Cardiac resynchronization therapies can include, but are not limited to, cardiac resynchronization therapy combined with pacing (CRT-P) and cardiac resynchronization therapy combined with defibrillation (CRT-D). Cardiac resynchronization therapy can be recommended based on an indication of an actual or potential heart failure. Some examples include a device that automatically begins CRT therapy. Some examples include devices that are upgradeable to provide CRT therapy. In some examples, a physician prescribes CRT therapy, and a device user programs an implanted device to provide CRT therapy. Some examples are configured to switch from a first CRT therapy to a second CRT therapy based on an indication of a heart failure or a potential heart failure provided by a system that monitors tachyarrhythmia and onset to tachyarrhythmia.

Figure 7A:
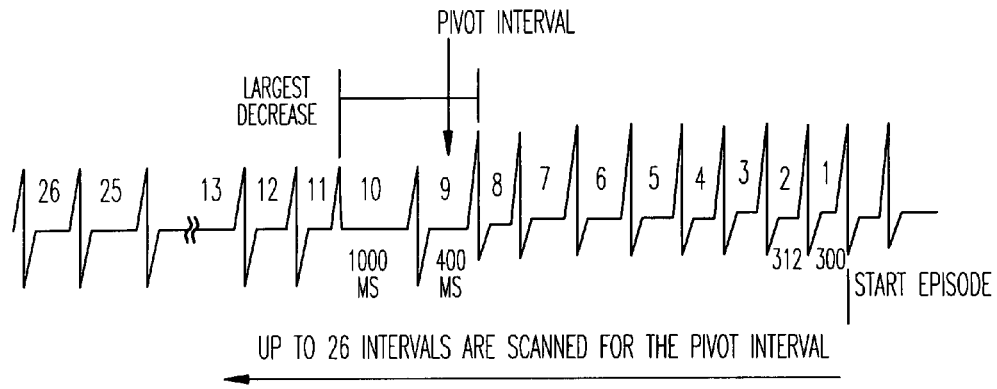
FIG. 7A shows a measured onset, according to one example.

FIGS. 7A-7D show a measured onset, according to one example. FIG. 7A shows a scanning window which includes a heart rate and an onset. The scan pictured in FIG. 7A includes up to 26 intervals. Some examples scan and analyze up to 32 intervals. Other numbers of intervals are possible. Examples such as the one illustrated proceed from right to left. In certain examples, the right of the scan is where a tachyarrhythmia episode commences. Some examples search multiple intervals and determine which two adjacent cycle lengths demonstrate the greatest decrease in cycle length. Of these two cycle lengths, the shorter length is established as a pivot interval.

Figure 7B:
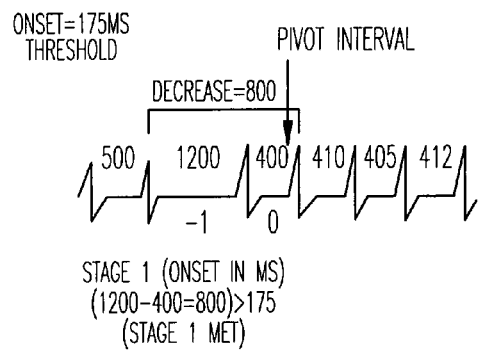
FIG. 7B shows a measured onset, according to one example.
Figure 7C:
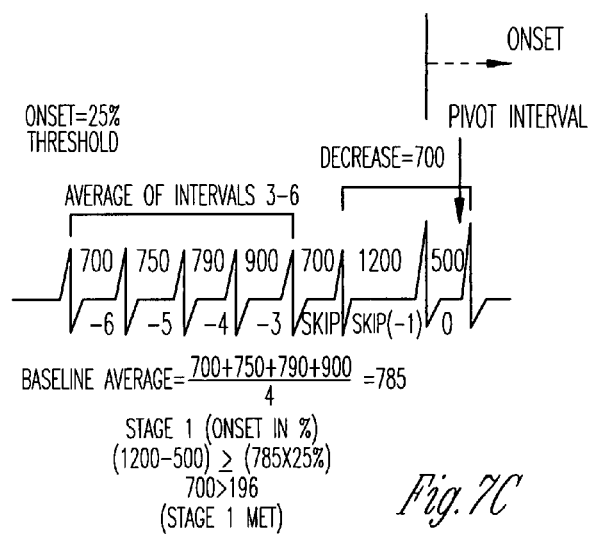
FIG. 7C shows a measured onset, according to one example.

Certain examples include multiple stages of onset classification. FIGS. 7B-C relate to a first stage of onset classification. The determination of how quickly onset occurs begins with finding a set of intervals in which a decrease in interval lengths between the intervals is sufficiently short to satisfy an onset initiation threshold. FIG. 7B shows an example in which a stage one temporal onset threshold of approximately 175 ms is established. In certain examples, a decrease of 800 ms is measured, which is in excess of the stage one temporal onset threshold of approximately 175 ms. As such, stage one is met. Other values for the onset threshold are possible.

Alternatively or in addition to the first stage one test, certain examples include a second stage one test, which can occur concurrent to the first stage one test. FIG. 7C illustrates such a test. Examples including such a test calculate a cycle length baseline (CLB) average. To calculate a CLB, the examples uses four of six intervals occurring before the pivot interval. In the example, the two intervals prior to the pivot interval are skipped to avoid counting premature ventricular contractions (PVCs) and compensatory pauses. The CLB is multiplied by a stage one percentage onset threshold. In some examples, such as the one illustrated, this value is approximately 25%. Other examples include a value which is approximately 17%. If the difference between the pivot interval and the interval preceding the pivot interval is greater than the CLB multiplied by the stage one percentage onset threshold, stage one onset is met.

In the example, a stage one onset is indicated as sudden if the pivot interval is greater than a stage one onset interval, or if the decrease from the pivot interval and the preceding interval is greater than the CLB multiplied by a stage one onset threshold percentage. If theses criterion are not met, the stage one onset is indicated as gradual. In some instances, if the onset is indicated as sudden, the technique proceeds to stage two.

Figure 7D:
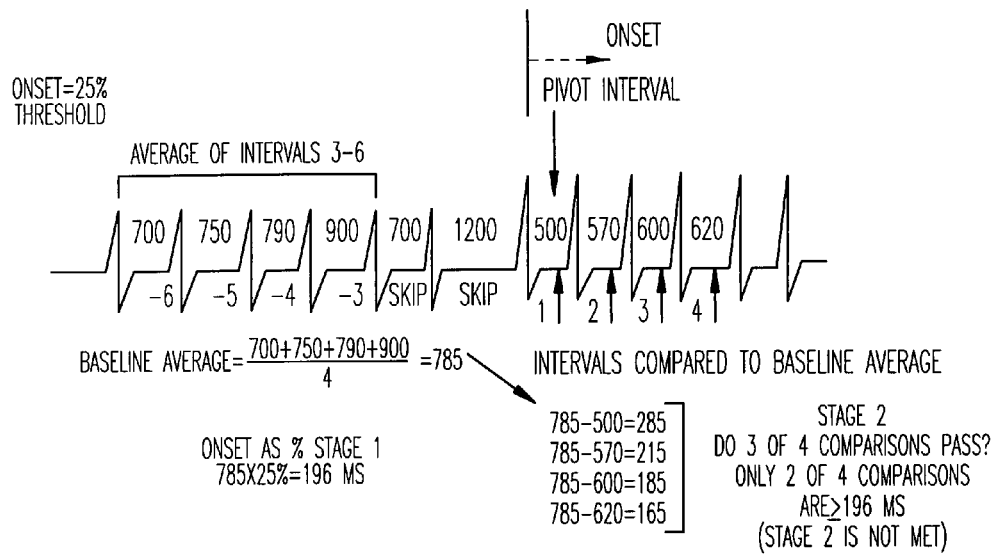
FIG. 7D shows a measured onset, according to one example.

Certain examples include a second stage of onset analysis. Some of those, such as the one illustrated in FIG. 7D, compare the CLB to each of four cycle lengths (CL(n)) beginning with the pivot interval. If the change in interval from the CLB to the CL(n) is over a stage two interval threshold in three out of the four cycle lengths, the stage two onset is indicated as sudden. Otherwise, the stage two onset is indicated as gradual. In various examples, the stage two interval threshold is the CLB multiplied by a percentage onset threshold. In certain examples, the stage two interval threshold is equivalent to the stage one percentage onset threshold multiplied by the CLB.

A final onset indication is communicated as sudden if both the stage one onset and the stage two are indicated as sudden. In various examples, the specified onset threshold is a final onset indication that is sudden, indicating that there is an onset threshold indicative of actual or potential heart failure.

Examples which do not require a sinus tachyarrhythmia to be detected are possible. For example, some configurations indicate actual or potential heart failure based on how quickly an onset to another type of tachyarrhythmia occurs. Some examples do not depend on a heart rate and instead indicate actual or potential heart failure based on how quickly an onset to a tachyarrhythmia occurs. These are other variations are contemplated.

In any of the examples described herein, processing described as being carried out by a particular one of the processor circuit can be carried out in whole or in part by another one or more of such elements. In many situations, it is desirable to communicate data from the implantable cardiac device to one or the local external interface device or the remote external interface device, such as to harness the processing power thereof, or to access historical data from the subject or from a population of other patients.

It is to be understood that the above description is intended to be illustrative, and not restrictive. For example, the above-described examples (or aspects thereof) may be used in combination with each other. Many other examples will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description, with each claim standing on its own as a separate example.

What is claimed is:
1. A method comprising:
monitoring a first heart rate; and
detecting a first sinus tachyarrhythmia episode preceded by the first heart rate;
when the first sinus tachyarrhythmia episode is detected:

determining how quickly a first onset to the first sinus tachyarrhythmia episode occurs by monitoring at least one time interval and calculating how quickly the first onset to the first sinus tachyarrhythmia episode occurs using the time interval; and automatically providing a congestive heart failure indication using information about the first heart rate and how quickly the first onset to the first sinus tachyarrhythmia episode occurs.

2. The method of claim 1, wherein automatically providing the congestive heart failure indication comprises using an indication that the first heart rate exceeds a specified threshold heart rate.

3. The method of claim 1, wherein the first heart rate immediately precedes first onset of the first sinus tachyarrhythmia episode.

4. The method of claim 1, wherein the automatically providing the congestive heart failure indication includes also using a clinically-obtained functional classification of the patient to determine the congestive heart failure indication.

5. The method of claim 1, comprising initiating or recommending a measurement of a respiratory rate of the patient in response to the congestive heart failure indication.

6. The method of claim 1, comprising initiating or recommending a measurement of an ejection fraction of the patient in response to the congestive heart failure indication.

7. The method of claim 1, comprising initiating or recommending a measurement of a B-type natriuretic peptide (BNP) of the patient in response to the congestive heart failure indication.

8. The method of claim 1, comprising initiating or recommending a measurement of a QRS width of the patient in response to the congestive heart failure.

9. The method of claim 1, comprising initiating or recommending a measurement of a heart rate variability of the patient in response to the congestive heart failure indication.

10. The method of claim 1, comprising measuring an indication of autonomic balance of the patient and wherein the automatically providing the congestive heart failure indication includes also using the measured indication of autonomic balance to determine the congestive heart failure indication.

11. The method of claim 10, comprising measuring heart rate variability of the patient and wherein the automatically providing the congestive heart failure indication includes also using the measured heart rate variability to determine the congestive heart failure indication.

12. The method of claim 1, wherein automatically providing a congestive heart failure indication uses an indication that the first onset occurs more quickly than a specified onset threshold.

13. The method of claim 12, comprising:
detecting a second sinus tachyarrhythmia episode preceded by a second heart rate;
determining a combined indication of the first and second heart rates;
determining a combined indication of how quickly onsets of the first and second sinus tachyarrhythmia episodes occur; and
automatically providing the congestive heart failure indication when the combined indication of the onsets occurs more quickly than the specified onset threshold and the combined indication of the first and second heart rates exceeds a specified threshold heart rate.

14. The method of claim 12, wherein the determining how quickly the first onset occurs includes determining an amount of change between a first cardiac cycle interval and a second cardiac cycle interval and further comprises: computing the indication that the first onset occurs more quickly than the specified onset threshold by comparing the amount of change between the first and second cardiac cycles to the specified threshold.

15. The method of claim 1, comprising monitoring a degree of pacing of a ventricle and automatically providing the congestive heart failure indication at least in part in response to at least one indication that the degree of pacing of the ventricle exceeds a specified degree of pacing threshold.

16. The method of claim 15, comprising automatically initiating, recommending, or monitoring a first cardiac resynchronization therapy.

17. The method of claim 16, comprising automatically providing a recommendation for a second cardiac resynchronization therapy.

18. An apparatus comprising:
a heart rate monitor circuit;
a sinus tachyarrhythmia episode detection circuit;
a sinus tachyarrhythmia onset detector circuit, configured to determine how quickly a first onset to the first sinus tachyarrhythmia episode occurs by monitoring at least one time interval and calculating how quickly the first onset to the first sinus tachyarrhythmia episode occurs using the time interval; and
a congestive heart failure indication detector circuit, coupled to at least one of the heart rate monitor circuit, the sinus tachyarrhythmia episode detection circuit, and the sinus tachyarrhythmia onset detector circuit,
wherein the congestive heart failure indication detector circuit is configured to provide a congestive heart failure indication when the first sinus tachyarrhythmia episode is detected, by using information about the first heart rate preceding the first sinus tachyarrhythmia episode and information about how quickly the first onset to the first sinus tachyarrhythmia episode occurs.

19. The apparatus of claim 18, wherein the heart rate monitor circuit is configured to be coupled to at least one external electrode.

20. The apparatus of claim 18, comprising a sinus tachyarrhythmia onset comparator circuit, configured to determine whether how quickly the first onset occurs exceeds a specified onset threshold.

21. The apparatus of claim 20, wherein the congestive heart failure indication detector circuit is configured to indicate an actual or potential congestive heart failure condition at least in response to at least one indication that the first onset occurs more quickly than the specified onset threshold.

22. The apparatus of claim 18, comprising a heart rate comparator circuit, configured to determine whether a first heart rate preceding the first onset of the first sinus tachyarrhythmia episode exceeds a specified heart rate threshold.

23. The apparatus of claim 18, wherein the apparatus includes an implantable medical device.

24. The apparatus of claim 23, wherein the heart rate monitor circuit is configured to be coupled to at least one implantable electrode.

25. The apparatus of claim 23, wherein the implantable medical device includes a wireless communication circuit configured to communicate information about the indicator to a local or remote external user interface.

26. The apparatus of claim 23, wherein the implantable medical device includes a cardiac rhythm management device including an electrostimulation delivery circuit that is configured to be controlled using information about the indicator.

27. An apparatus comprising:
   a heart rate monitor circuit configured to detect a first heart rate and a second heart rate;
   a sinus tachyarrhythmia episode detection circuit configured to detect a first sinus tachyarrhythmia episode preceded by the first heart rate, and to detect a second sinus tachyarrhythmia episode preceded by the second heart rate;
   means for determining how quickly a first onset to the first sinus tachyarrhythmia episode occurs by monitoring at least one time interval and calculating how quickly the first onset to the first sinus tachyarrhythmia episode occurs using the time interval; and
   means for automatically providing a congestive heart failure indication using an indication that the first onset occurs more quickly than a specified onset threshold together with an indication that a first heart rate exceeds a specified threshold heart rate, wherein the first heart rate precedes the first onset to the first sinus tachyarrhythmia episode.

28. The apparatus of claim 27, wherein the means for determining how quickly a first onset to the first sinus tachyarrhythmia episode occurs includes a heart rate comparator circuit, configured to determine whether a first heart rate preceding the first onset of the first sinus tachyarrhythmia episode exceeds a specified threshold heart rate value.

29. The apparatus of claim 27, wherein the means for automatically providing a congestive heart failure indication includes an indicator, coupled to at least one of a sinus tachyarrhythmia onset detector circuit and a heart rate monitor circuit, the indicator configured to indicate the actual or potential congestive heart failure condition at least in response to at least one indication that the first onset occurs more quickly than a specified onset threshold together with at least one indication the first heart rate exceeds a specified threshold heart rate.

30. A method comprising:
   monitoring a first heart rate; and
   detecting a first sinus tachyarrhythmia episode preceded by the first heart rate;
   when the first sinus tachyarrhythmia episode is detected:
      determining how quickly a first onset to the first sinus tachyarrhythmia episode occurs; and
      automatically providing an indication of an actual or potential congestive heart failure condition using information about the first heart rate and how quickly the first onset to the first sinus tachyarrhythmia episode occurs,
      wherein automatically providing an indication of an actual or potential congestive heart failure condition uses an indication that the first onset occurs more quickly than a specified onset threshold;
   detecting a second sinus tachyarrhythmia episode preceded by a second heart rate;
   determining a combined indication of the first and second heart rates;
   determining a combined indication of how quickly onsets of the first and second sinus tachyarrhythmia episodes occur; and
   automatically providing the indication of the congestive heart failure condition when the combined indication of the onsets occurs more quickly than the specified onset threshold and the combined indication of the first and second heart rates exceeds a specified threshold heart rate.

31. A method comprising:
   monitoring a first heart rate; and
   detecting a first sinus tachyarrhythmia episode preceded by the first heart rate;
   when the first sinus tachyarrhythmia episode is detected:
      determining how quickly a first onset to the first sinus tachyarrhythmia episode occurs; and
      automatically providing a congestive heart failure indication using information about the first heart rate and how quickly the first onset to the first sinus tachyarrhythmia episode occurs, wherein automatically providing a congestive heart failure indication uses an indication that the first onset occurs more quickly than a specified onset threshold;
   detecting a second sinus tachyarrhythmia episode preceded by a second heart rate;
   determining a combined indication of the first and second heart rates;
   determining a combined indication of how quickly onsets of the first and second sinus tachyarrhythmia episodes occur; and
   automatically providing the congestive heart failure indication when
      the combined indication of how quickly onsets of the first and second sinus tachyarrhythmia episodes occur indicates that the onsets of the first and second sinus tachyarrhythmia episodes occur more quickly than the specified onset threshold, and
      the combined indication of the first and second heart rates exceeds a specified threshold heart rate.

* * * * *